United States Patent [19]

Matsuura et al.

[11] 4,277,257
[45] Jul. 7, 1981

[54] PROCESS FOR PREVENTING SCALE DEPOSITION

[75] Inventors: Ryo Matsuura, Yamato; Katsumi Matsuzaki; Masao Narita, both of Yokohama, all of Japan

[73] Assignee: Kawasaki Kasei Chemicals Ltd., Tokyo, Japan

[21] Appl. No.: 95,522

[22] Filed: Nov. 19, 1979

[30] Foreign Application Priority Data

Feb. 16, 1979 [JP] Japan .................................. 54-17545

[51] Int. Cl.$^3$ ............................................. B01D 47/00
[52] U.S. Cl. ......................................... 55/85; 260/707; 260/DIG. 35; 562/408; 562/485
[58] Field of Search ............................. 55/84-95; 260/346.4, 396 R, 707, DIG. 35; 562/408, 485

[56] References Cited

U.S. PATENT DOCUMENTS

| 3,370,400 | 2/1968 | Hoffman et al. | 55/94 |
| 3,379,741 | 4/1968 | Tschamper et al. | 562/485 |

FOREIGN PATENT DOCUMENTS 53-9209  4/1978  Japan .

*Primary Examiner*—Bernard Nozick
*Attorney, Agent, or Firm*—Oblon, Fisher, Spivak, McClelland & Maier

[57] ABSTRACT

A scale deposition from an aqueous slurry of naphthoquinone and phthalic acid can be prevented by adding fine crystals of phthalic acid to the aqueous slurry of naphthoquinone and phthalic acid collected, which slurry is obtained by contacting a gas resulting from a catalytic gas phase oxidation of naphthalene with water or a mother liquor recycled. The fine crystals of phthalic acid have diameters of less than 100μ, preferably 10 to 40μ, and can be in an aqueous slurry of phthalic acid pulverized by a pulverizer.

5 Claims, 1 Drawing Figure

PROCESS FOR PREVENTING SCALE DEPOSITION

BACKGROUND OF THE INVENTION

FIELD OF THE INVENTION

The present invention relates to a process for preventing scale deposition in a water washing type collector and pipe line instruments thereof in an operation for feeding a gas obtained by a catalytic gas phase oxidation of naphthalene into the water washing type collector to collect naphthoquinone and phthalic anhydride in the gas as a slurry of naphthoquinone and phthalic acid with an aqueous medium.

It has been known to use an atomizer, a scrubber or a bubble tower as a water washing type collector for collecting napthoquinone and phthalic anhydride from a gas obtained by a catalytic gas phase oxidation of naphthalene by washing with an aqueous medium by an industrial operation. In the conventional process, scale is deposited in a water washing type collector and pipe line instruments thereof, so as to form a deposited layer having a thickness of several tens to several hundreds mm and to decrease an effective capacity of the collector and the pipe line instruments. The scale is peeled off and accumulated in the tower and the vessel and is flowed into the pipe and a pump whereby the flow rate becomes irregular and the devices are clogged. Thus, serious troubles are caused such as the continuous operation can not be carried out and the devices are damaged. It has been well-known that the scale deposition in the water washing collector and the pipe line instruments thereof causes serious industrial disadvantages (such as Japanese Patent Publication No. 9209/1978). Moreover, a large amount of naphthoquinone remains as the scale in the devices so as to cause inferior yield of naphthoquinone. Thus, the scale should be peeled out and naphthoquinone should be recovered. However, the solubility of naphthoquinone in water is relatively low and naphthoquinone is easily decomposed by heat or an alkaline solution, and accordingly, the dissolution and the separation by using hot water or an alkaline aqueous solution is industrially difficult and disadvantageous. Moreover, naphthoquinone causes irritation of skin and accordingly, a manual operation for discharging scale containing a large amount of naphthoquinone is quite difficult. Thus, when the separation of the scale is indispensable, the scrubber and the recycling system should be washed with an alkaline aqueous solution. In the separation, the operation would be interrupted disadvantageously.

It has been proposed to improve the separation of the scale deposition as follows.

(1) The collection is carried out as an aqueous solution of a monophthalate having pH of 3 to 5 by adding a base in a solution for water washing (Japanese Patent Publication No. 9209/1978).

(2) The collection is carried out by using a dilute aqueous solution of phthalic acid or an aqueous solution of maleic acid.

The process (1) is not economical because a base is used and an acid for neutralization is required for recovering phthalic acid. The process (2) is not practically employed because a large amount of the aqueous solution is formed.

The inventors have studied the reason why the scale deposition is caused in detail in order to prevent the scale deposition in the water washing collector and the pipe line instruments thereof and to maintain the stable operation of the collector.

According to the analysis of the scale deposited, it has been found that more than 90% of the total component of the scale is naphthoquinone even though naphthoquinone and phthalic acid are in the form of an aqueous slurry.

According to an analysis of components dissolved in a filtrate obtained by a filtration of the aqueous slurry, it has been found that the filtrate is in a supersaturated condition, that phthalic acid and naphthoquinone are dissolved over their solubilities at the temperature, and the scale deposition caused is substantially proportional to the supersaturated degree.

The inventors have studied to reduce the supersaturated degree in view of the above-mentioned findings. That is, various tests have been made by adding various additives to the aqueous slurry containing naphthoquinone and phthalic acid obtained by the water washing collection. It has been found that there is substantially no effect by an addition of fine powdery naphthoquinone but when a fine powdery phthalic acid is added, the supersaturated degree of phthalic acid and naphthoquinone dissolved in the liquid phase could be decreased even though solid phthalic acid is in the slurry.

Thus, a fine powdery phthalic acid in a slurry form is added to the slurry in the water washing type collector, whereby the supersaturated degree is decreased and the scale deposition in the apparatus could be substantially prevented. The present invention has been completed by the findings.

SUMMARY OF THE INVENTION

It is an object of the present invention to provide a process for preventing scale deposition in a process for collecting naphthoquinone and phthalic anhydride obtained by a catalytic gas phase oxidation of naphthalene, by a water washing type collector.

The foregoing and other objects of the present invention have been attained by providing a process for preventing scale deposition in a water washing type collector and pipe line instruments thereof for collecting naphthoquinone and phthalic anhydride from a gas obtained by a catalytic gas phase oxidation of naphthalene as an aqueous slurry of naphthoquinone and phthalic acid which comprises feeding the gas containing naphthoquinone and phthalic anhydride obtained by the catalytic gas phase oxidation into the water washing type collector to contact the gas with the aqueous medium incorporating a fine powdery phthalic acid so as to decrease the supersaturated degrees of phthalic acid and naphthoquinone dissolved in the liquid phase.

DETAILED DESCRIPTION OF THE PREFERRED EMBODIMENTS

Figure 1:
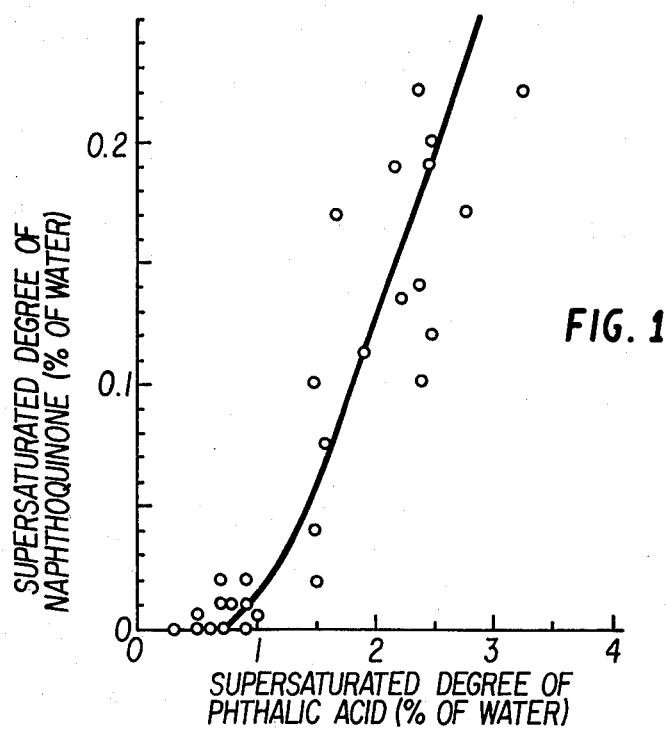
FIG. 1 is a graph showing the relation of the supersaturated degree of naphthoquinone and the supersaturated degree of phthalic acid.

The catalytic gas phase oxidation of naphthalene is usually carried out on a vanadium oxide-potassium sulfate catalyst in an industrial operation. The resulting gas containing naphthoquinone and phthalic anhydride is usually passed through a heat-exchanging boiler and a cooler to cool it at 180° to 300° C. and it is fed into the water washing type collector. The water washing type collector can be an atomizer type collector (Japanese Patent Publication No. 29298/1970), a scrubber (Japanese Patent Publication No. 9209/1978) or a bubble tower. The collection of the resulting gas in the water washing type collector is carried out at 30° to 70° C. usually 40° to 60° C.

In the water washing type collector, the resulting gas contacts with the aqueous medium to be cooled to said temperature and naphthoquinone and phthalic anhydride in the resulting gas are collected as an aqueous slurry of naphthoquinone and phthalic acid and the non-absorbed gas is discharged after washing the gas. Then, the aqueous slurry is treated by a known process such as a solvent extraction so as to separate it into naphthoquinone and an aqueous solution of phthalic acid. Naphthoquinone is recovered by a distillation of the solvent whereas phthalic acid is recovered by a crystallization by cooling.

In the process of the present invention, the fine crystals of phthalic acid added to the aqueous slurry can be a pure phthalic acid obtained by a hydration of purified phthalic anhydride. In the industrial operation, a part of the crystallized phthalic acid is preferably recycled. It is also possible to use phthalic acid obtained by pulverizing the phthalic acid in the aqueous slurry in a water washing type collector. Both of the methods can be combined.

The particle size of fine crystals of phthalic acid is usually less than $100\mu$ preferably in a range of 10 to $40\mu$ since a large quantity of the fine crystals is required in the case of large particle size. Thus, the quantity of the fine crystals can not be reduced even though the particle size of the fine crystals is further decreased.

The crystals of the phthalic acid in the aqueous slurry in the water washing type collector are usually not suitable to use them as seeds and should be pulverized by a desired wet type pulverizer.

The amount of the fine crystals of the phthalic acid added to the aqueous slurry is dependent upon pH and components of the aqueous slurry, particle size of the fine crystals of phthalic acid and temperature.

It is preferable to achieve less than 1% of a supersaturated degree of the phthalic acid dissolved in the aqueous slurry (the value obtained by subtracting solubility of phthalic acid at the temperature from the concentration of phthalic acid in the liquid phase (g/100 g of water); this is shown by percent). That is, the supersaturated degree of naphthoquinone in the liquid phase (the value is shown in the same manner as that of phthalic acid) is suddenly decreased depending upon the decrease of the supersaturated degree of phthalic acid. When the supersaturated degree of phthalic acid is decreased to 1.5% preferably less than 1%, the supersaturated degree of naphthoquinone is substantially decreased to 0 to 0.02%. In such condition, the scale deposition in the water washing type collector and the pipe line instruments thereof can be completely prevented. In the condition causing the scale deposition, the particle size of the crystals in the aqueous slurry in the water washing type collector is usually large such as greater than 2 to 3 mm of diameter. The large particles are deposited in the water washing type collector and the pipe line instruments thereof so as to cause trouble in the discharge of the aqueous slurry collected by the water washing.

In accordance with the process of the present invention adding the fine crystals of phthalic acid to the aqueous slurry for the water washing, it is also possible to prevent the formation of large crystals in the aqueous slurry for the water washing.

The industrial process of the present invention can be carried out as follows.

The gas containing naphthoquinone, phthalic anhydride, maleic anhydride, sulfur trioxide and the unreacted naphthalene which is obtained by the catalytic gas phase oxidation of naphthalene is cooled to about 180° to 300° C. and is fed into a scrubber water washing type collector such as a spraying tower or a bubbling tower and is usually contacted with a collecting water at 30° to 70° C. so as to collect them as an aqueous slurry of phthalic acid and naphthoquinone, each at concentration of 1 to 30 wt.%. A constant quantity of the aqueous slurry is held at the bottom of the collector tower. A part of the aqueous slurry is discharged and treated by the conventional separation of naphthoquinone and phthalic acid, for example, the process for extracting naphthoquinone with an organic solvent such as toluene and xylene by heating the discharged aqueous slurry to separate naphthoquinone from the water phase containing phthalic acid and crystallizing phthalic acid by cooling the water phase and filtering it. The filtrate is recycled as the collecting water. Before the recycling, it is preferable to neutralize sulfuric acid and maleic acid.

When the spray tower is used as the water washing type collector, a part of the aqueous slurry should be fed to the spray at the top of the collecting tower by a pump and the aqueous slurry in the collecting tower should be stirred.

In such water washing type collector, the pipe, the pump etc., the scale deposition is immediately initiated when the process of the present invention is not applied. Thus, the fine crystals of phthalic acid should be added so as to decrease the supersaturated degrees of phthalic acid and naphthoquinone in the aqueous slurry held in the collector. The fine crystals of phthalic acid can be added in a form of powder, however the fine crystals are preferably added as an aqueous slurry, for example, the slurry obtained by suspending the fine crystals of phthalic acid in the filtrate or water or the slurry obtained by pulverizing phthalic acid in the aqueous slurry in the water washing type collector.

The concentration of the slurry of phthalic acid can be the concentration for the fluidizable condition and is usually in a range of 1 to 30 wt.% preferably 3 to 20 wt.%. The position for the addition can be any position in the water washing type collector, for example, at the part holding the aqueous slurry at the bottom of the water washing type collector.

As described above, in accordance with the process of the present invention, the trouble of the scale deposition in the water washing type collector and pipe line equipments thereof in the collection of the gas obtained by the catalytic gas phase oxidation of naphthalene can be easily and completely prevented, and also the formation of large crystals in the resulting aqueous slurry can be prevented, and the defect of the discharge of the aqueous slurry can be prevented. Thus, it is possible to attain unthinkable industrial advantages.

The present invention will be further illustrated by certain examples and references which are provided for purposes of illustration only and are not intended to be limiting the present invention.

In the specification, the terms "%" and "part" means "% by weight" and "part by weight", unless otherwise defined.

EXAMPLE 1

A gas obtained by a catalytic gas phase oxidation of naphthalene (naphthoquinone at a rate of 1.0 part/hour; phthalic anhydride at a rate of 1.7 parts/hour; maleic anhydride at a rate of 0.02 part/hour; sulfur trioxide at a rate of 0.02 part/hour and the unreacted naphthalene at a rate of 0.02 part/hour) was passed through a heat exchanger at a rate of 80 parts/hour to cool it to 250° C. and was fed into a bubbling tower water washing type collector at an operation temperature of 50° to 60° C. (average of 56° C.) whereby the gas was washed and collected.

In the collector, the mother liquor containing 1% of phthalic acid and 1% of maleic acid obtained by a separation from phthalic acid crystals was fed at a rate of 38 parts/hour. An aqueous slurry containing 8% of fine crystals of phthalic acid (more than 50% of phthalic acid crystals are particles having diameters of less than 40$\mu$) was fed at 4 parts/hour to the part holding the aqueous slurry at the bottom of the collector, whereby the supersaturated degree of phthalic acid was held to less than 1% in the aqueous medium. The aqueous slurry in the collector was discharged at a ratio corresponding to the feed of the reaction gas, and naphthoquinone was extracted with xylene by a counter-current extraction at 85° C. The separated water phase was cooled to 30° C. to crystallize phthalic acid. The phthalic acid crystals were separated by a filtration and the mother liquor (filtrate) was recycled after neutrallizing sulfuric acid component, to the collector. A part of the mother liquor was used for preparing the aqueous slurry of fine crystals of phthalic acid.

Figure 2:
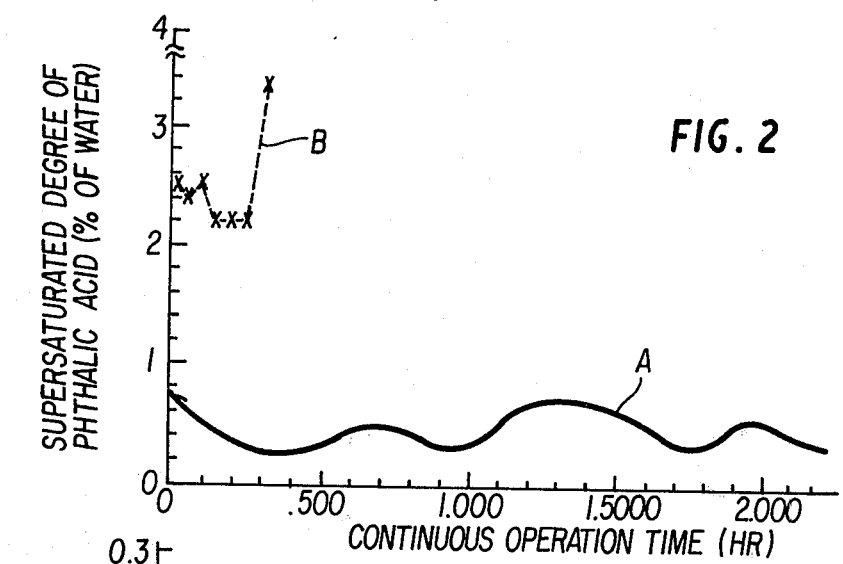
FIG. 2 is a graph showing the supersaturated degree of phthalic acid in the time of the continuous operation.
Figure 3:
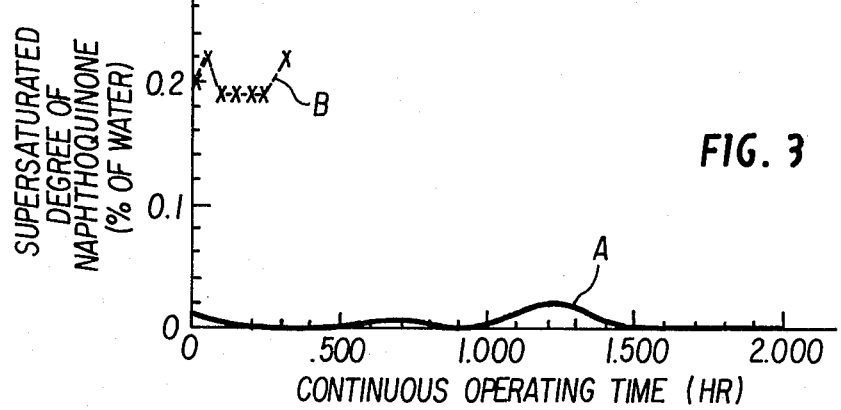
FIG. 3 is a graph showing the supersaturated degree of naphthoquinone in the time of the continuous operation. Curve A . . . Example 1 of the process of the present invention Curve B . . . Reference 1 of the conventional process.

The results of the continuous operation for 2,200 hours are shown in FIGS. 2 and 3. The solubilities of phthalic acid and naphthoquinone were respectively 2.8 g/100 g of water and 0.19 g/100 g of water in this example.

As shown in FIG. 2A, the supersaturated degree of phthalic acid was less than 1% and as shown in FIG. 3A, the supersaturated degree of naphthoquinone was less than 0.02%. Thus, a scale deposition was not substantially found in any part of the water washing type collector, the pipe lines for the aqueous slurry and the pump. A defect of discharge of the aqueous slurry caused by peeling off the scale was not also found. The crystals of phthalic acid and naphthoquinone in the aqueous slurry had particle size of 20 to 60$\mu$ whereby no trouble was caused in the transferring of the aqueous slurry. The supersaturated degrees shown in FIGS. 2 and 3 respectively are the values obtained by subtracting each solubility from each quantity of phthalic acid or naphthoquinone dissolved in the mother liquor of the aqueous slurry.

COMPARATIVE EXAMPLE 1

In accordance with the process of Example 1 except that the aqueous slurry of fine crystals of phthalic acid (8%) was not fed to the collector, the continuous operation was carried out 360 hours. The results are shown in FIGS. 2 and 3. The supersaturated degree of phthalic acid in the solution of the aqueous slurry was 2.2 to 3.3% (FIG. 2B) and the supersaturated degree of naphthoquinone was 0.19 to 0.22% (FIG. 3B). In the collector, a scale was deposited in a thickness of 50 to 200 mm. The scale was formed also in the pipes for passing the aqueous slurry. On the other hand, the crystals in the aqueous slurry had diameters of 2 to 3 mm. The large crystals deposited in the collector and the outlet system for the aqueous slurry caused defect of the discharge. The pipes were clogged by the peeled scale to cause the difficulty of the continuation of the operation. The operation could not be continued in practice.

We claim:

1. In a process for preventing scale deposition in a water washing type collector and pipe line instruments thereof for collecting naphthoquinone and phthalic anhydride in an aqueous slurry from a gas obtained by a catalytic gas phase oxidation of naphthalene, the improvement characterized by adding fine crystals of phthalic acid to the aqueous slurry to decrease supersaturated degrees of phthalic acid and naphthoquinone in the liquid phase.

2. A process according to claim 1 wherein the fine crystals of phthalic acid are added to the aqueous slurry of naphthoquinone and phthalic acid so as to decrease the supersaturated degree of phthalic acid to less than 1.5%.

3. A process according to claim 1 wherein said fine crystals of phthalic acid have diameters of less than 100$\mu$.

4. A process according to claim 1 wherein said fine crystals of phthalic acid have diameters in a range of 10 to 40$\mu$.

5. A process according to claim 1 wherein said fine crystals of phthalic acid are obtained by pulverizing the phthalic acid in the aqueous slurry of naphthoquinone and phthalic acid and/or the phthalic acid which is crystallized after extracting naphthoquinone from the aqueous slurry.

* * * * *